(12) United States Patent
Chaudhry et al.

(10) Patent No.: US 8,221,740 B2
(45) Date of Patent: Jul. 17, 2012

(54) SIDE POPULATION CELLS IN CARDIAC REPAIR

(75) Inventors: Hina W. Chaudhry, New York, NY (US); Debra J. Wolgemuth, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 11/535,444

(22) Filed: Sep. 26, 2006

(65) Prior Publication Data

US 2007/0178075 A1     Aug. 2, 2007

Related U.S. Application Data

(60) Provisional application No. 60/720,765, filed on Sep. 26, 2005.

(51) Int. Cl.
| | | |
|---|---|---|
| *A61K 48/00* | (2006.01) | |
| *A61K 43/04* | (2006.01) | |
| *A01N 63/00* | (2006.01) | |
| *A01N 43/04* | (2006.01) | |

(52) U.S. Cl. ................. 424/93.21; 514/44; 514/93.2
(58) Field of Classification Search ............... 424/93.1, 424/93.21, 93.2; 514/44
See application file for complete search history.

(56) References Cited

U.S. PATENT DOCUMENTS

| | | | |
|---|---|---|---|
| 5,973,119 A | 10/1999 | Coats et al. | |
| 6,150,584 A | 11/2000 | Kucherlapati et al. | |
| 6,162,963 A | 12/2000 | Kucherlapati et al. | |
| 6,278,039 B1 | 8/2001 | Johnson et al. | |
| 6,309,370 B1 | 10/2001 | Haim et al. | |
| 6,448,080 B1 | 9/2002 | Ward et al. | |
| 6,491,905 B1 | 12/2002 | Sorscher et al. | |
| 6,534,052 B1 | 3/2003 | Xiao et al. | |
| 7,097,833 B2 * | 8/2006 | Freyman .................. 424/93.7 |
| 2002/0006664 A1 | 1/2002 | Sabatini et al. | |
| 2002/0166134 A1 | 11/2002 | Field et al. | |
| 2002/0197240 A1 | 12/2002 | Chiu | |
| 2003/0017549 A1 | 1/2003 | Owens | |
| 2003/0022367 A1 | 1/2003 | Xu et al. | |
| 2003/0054973 A1 | 3/2003 | Anversa | |
| 2003/0229202 A1 | 12/2003 | Guo et al. | |
| 2004/0014213 A1 | 1/2004 | Freyman | |
| 2006/0160733 A1 | 7/2006 | Chaudhry | |

FOREIGN PATENT DOCUMENTS

| | | |
|---|---|---|
| WO | 99/32619 | 7/1999 |
| WO | 01/29058 | 4/2001 |
| WO | 01/68836 | 9/2001 |
| WO | 01/96584 | 12/2001 |

OTHER PUBLICATIONS

Murphy (Nature Genetics 15:83-86; 1997).*
Haddad (BBRC 274:188-196; 2000).*
Thomas (Nature Rev. Genet. 4: 346-358; 2003).*
Woo (Circulation, 2006, vol. 114, Suppl. I, p. I-206-I-213).*
Miller 1995, FASEB J., vol. 9, p. 190-199.*
Deonarain, 1998, Expert Opin. Ther. Pat., vol. 8, p. 53-69.*
Verma, Sep. 1997, Nature, vol. 389, p. 239-242.*
Crystal, 1995, Science, vol. 270, p. 404-410, p. 409.*
Ross, Sep. 1996, Human Gene Therapy, vol. 7, p. 1781-1790.*
Challen (Stem Cells, 2006, vol. 24, p. 3-12).*
Asakura A and Rudnicki MA, Side population cells from diverse adult tissues are capable of in vitro hematopoietic differentiation, Exp. Hematol., 2002, p. 1339-45, vol. 30(11).
Asakura A, et al., Myogenic specification of side population cells in skeletal muscle, J. Cell. Biol., 2002, p. 123-34, vol. 159(1).
Balsam LB, et al., Haematopoietic stem cells adopt mature haematopoietic fates in ischaemic myocardium, Nature, 2004, p. 668-73, vol. 428(6983).
Chaudhry HW, et al., Cyclin A2 mediates cardiomyocyte mitosis in the postmitotic myocardium, J. Biol. Chem., 2004, p. 35858-66, vol. 279(34).
Gussoni E, et al., Dystrophin expression in the mdx mouse restored by stem cell transplantation, Nature, 1999, p. 390-4, vol. 401(6751).
Jackson KA, et al., Hematopoietic potential of stem cells isolated from murine skeletal muscle, PNAS, 1999, p. 14482-6, vol. 96(25).
Jackson KA, et al., Regeneration of ischemic cardiac muscle and vascular endothelium by adult stem cells, J. Clin. Invest., 2001, p. 1395-402, vol. 107(11).
Martin CM, et al., Persistent expression of the ATP-binding cassette transporter, Abcg2, identifies cardiac SP cells in the developing and adult heart, Dev. Biol., 2004, p. 262-75, vol. 265(1).
Murry CE, et al., Haematopoietic stem cells do not transdifferentiate into cardiac myocytes in myocardial infarcts, Nature, 2004, p. 664-8, vol. 428(6983).
Nygren JM, et al., Bone marrow-derived hematopoietic cells generate cardiomyocytes at a low frequency through cell fusion, but not transdifferentiation, Nat. Med., 2004, p. 494-501, vol. 10(5).
Orlic D, et al., Bone marrow cells regenerate infarcted myocardium, Nature, 2001, p. 701-5, vol. 410(6829).
Orlic D, et al., Mobilized bone marrow cells repair the infarcted heart, improving function and survival, PNAS, 2001, p. 10344-9, vol. 98(18).
Yoshizumi M, et al., Disappearance of cyclin A correlates with permanent withdrawal of cardiomyocytes from the cell cycle in human and rat hearts, J. Clin. Invest., 1995, p. 2275-80, vol. 95(5).
International Search Report—PCT/US06/37443, Feb. 5, 2008, International Searching Authority.
Poolman et al, Cell cycle profiles and expressions of p21CIP1 and p27KIP1 during myocyte development, Int J Cardiol, 1998, 67:133-142.
Poss et al, Heart regeneration in zebrafish, Science, 2002, 298:2188-2190.
Quelle et al, Overexpression of mouse D-type cyclins accelerates G1 phase in rodent fibroblasts, Genes Dev, 1993, 8:1559-1571.

(Continued)

*Primary Examiner* — Michael C. Wilson
(74) *Attorney, Agent, or Firm* — SNR Denton US LLP

(57) ABSTRACT

It has been discovered that side-population cells induce cardiac tissue repair of infarcted myocardium. Provided herein are methods directed to treatment of cardiac injury using side-population cells.

9 Claims, 8 Drawing Sheets

OTHER PUBLICATIONS

Ravnik and Wolgemuth, The developmentally restricted pattern of expression in the male germ line of a murine cyclin A, cyclin A2, suggests roles in both mitotic and meiotic cell cycles, Dev Biol, 1996, 173:69-78.

Reiss et al, Myocardial infarction is coupled with activation of cyclins and cyclin-dependent kinases in myocytes, Exp Cell Res, 1996, 225:44-54.

Sherr and Roberts, Inhibitors of mammalian G1 cyclin-dependent kinases, Genes Dev, 1995, 9:1194-1163.

Simpson, Proto-oncongenes and cardiac hypertrophy, Annu Rev Physiol, 1989, 51:189-202.

Slawson et al, Cardiac MRI of the normal and hypertrophied mouse heart, Magn Reson Med, 1998, 39:980-987.

Soonpaa and Field, Survey of studies examining mammalian cardiomyocyte DNA synthesis, Circ Res, 1998, 83:15-26.

Soonpaa et al, Cyclin D1 overexpression promotes cardiomyocyte DNA synthesis and multinucleation in transgenic mice, J Clin Invest, 1997, 99:2644-2654.

Speir et al, Acidic and basic fibroblast growth factors in adult rat heart myocytes. Localization, regulation in culture, and effects on DNA synthesis, Circ Res, 1992, 71:251-259.

Stein and Cohen, Oligodeoxynucleotides as inhibitors of gene expression: a review, Cancer Res, 1998, 48:2659-2668.

Strauer et al, Repair of infarcted myocardium by autologous intracoronary mononuclear bone marrow cell transplantation in humans, Circulation, 2002, 106:1913-1918.

Subramaniam et al, Tissue-specific regulation of the alpha-myosin heavy chain gene promoter in transgenic mice, J Biol Chem, 1991, 266:24613-24620.

Sweeney et al, A distinct cyclin A is expressed in germ cells in the mouse, Development, 1996, 122:53-64.

Tang et al, In vivo determination of body composition of rats using magnetic resonance imaging, Ann NY Acad Sci, 2000, 904:32-41.

Tavian et al, Stable expression of antisense urokinase mRNA inhibits the proliferation and invasion of human hepatocellular carcinoma cells, Cancer Gene Ther, 2003, 10:112-120.

Tse et al, Angiogenesis in ischaemic myocardium by intramyocardial autologous bone marrow mononuclear cell implantation, Lancet, 2003, 361:47-49.

Wei et al, Inhibition of Rho family GTPases by Rho GdP dissociation inhibitor disrupts cardiac morphogenesis and inhibits cardiomyocyte proliferation, Development, 2002, 7:1705-1714.

Wei et al, Phosphorylation of histone H3 at serine 10 is correlated with chromosome condensation during mitosis and meiosis in Tetrahymena, PNAS, 1998, 95:7480-7484.

Wiesmann et al, Developmental changes of cardiac function and mass assessed with MRI in neonatal, juvenile and adult mice, Am J Physiol, 2000, 278:H653-657.

Wilda et al, Killing of leukemic cells with a BCR/ABL fusion gene RNA interference (RNAi), Oncogene, 2002, 21:5716-5724.

Zhang et al, An anti-sense construct of full-length AIM cDNA imposes a radiosensitive phenotype on normal cells, Oncogene, 1998, 17:811-818.

Zhou et al, The ABC transporter Bcrp1/ABCG2 is expressed in a wide variety of stem cells and is a molecular determinant of the side-population phenotype, Nat Med, 2001, 7:1028-1034.

Supplementary European Search Report issued Jun. 19, 2009, in the related application EP 04752668.

Engel et al, p21CIP1 controls proliferating cell nuclear antigen level in adult cardiomyocytes, Molecular and Cellular Biology, 2003, 23:555-565.

Agah et al, Adenoviral delivery of E2F-1 directs cell cycle reentry and p53-independent apoptosis in postmitotic adult myocardium in vivo, J Clin Invest, 1997, 100:2722-2728.

Ashrafi et al, Genome-wide RNAi analysis of *Caenorhabditis elegans* fat regulatory genes, Nature, 2003, 421:268-272 (abstract only).

Assmus et al, Transplantation of progenitor cells and regeneration enhancement in acute myocardial infarction (TOPCARE-AMI) Circulation, 2002, 106:3009-3017.

Behringer et al, Sequences 5' of the homeobox of the Hox-1.4 gene direct tissue-specific expression of IacZ during mouse development, Development, 1993, 117:823-833.

Beinlich and Morgan, Control of growth in neonatal pig hearts, Mol Cell Biochem, 1993, 119:3-9.

Beltrami et al, Adult cardiac stem cells are multipotent and support myocardial regeneration, Cell, 2003, 114:763-76.

Fefer, "Special delivery" to cancer cells, Blood, 2002, 99:1503-1504.

Ghosh et al, Role of superoxide dismutase in survival of Leishrnania within the macrophage, Biochem J, 2003, 369:447-452.

Haracska et al, Stimulation of DNA synthesis activity of human DNA polymerase kappa by PCNA, Mol Cell Biol, 2002, 3:784-791.

Hendzel et al, Mitosis-specific phosphorylation of histone H3 initiates primarily within pericentromeric heterochromatin during G2 and spreads in an ordered fashion coincident with mitotic chromosome condensation, Chromosome, 1997, 106:348-360.

Huser et al, Incorporation of decay-accelerating factor into the baculovirus envelope generates complement-resistant gene transfer vectors, Nat Biotechnol, 2001, 19:451-455.

Jackson et al, The c-myc proto-oncogene regulates cardiac development in transgenic mice, Mol Cell Biol, 1990, 7:3709-3716.

Kajstura et al, Telomere shortening is an in vivo marker of myocyte replication and aging, Am J Pathol, 2000, 156:813-819.

Kim et al, Cell cycle regulators during human atrial development, Korean J Intern Med, 1998, 13:77-82.

Kirshenbaum and Schneider, Adenovirus E1A represses cardiac gene transcription and reactivates DNA synthesis in ventricular myocytes via alternative pocket protein- and p300-binding domains, J Biol Chem, 1995, 270:7791-7794.

Kocher et al, Neovascularization of ischemic myocardium by human bone-marrow-derived angioblasts prevents cardiomyocyte apoptosis, reduced remodeling and improves cardiac function, Nat Med, 2001, 7:430-436.

Kwong et al, The suppression of colon cancer cell growth in nude mice by targeting beta-catenin/TCF pathway, Oncogene, 2002, 21:8340-8346.

Laugwitz et al, Postnatal ils1+ cardioblasts enter fully differentiated cardiomyocyte lineages, Nature, 2005, 433:647-653 (abstract only).

Leri et al, Telomerase Activity in Rat Cardiac Myocytes is Age and Gender Dependent, Mol Cell Cardiol, 2000, 32:385-390 (abstract only).

Li et al, Rapid Transition of Cardiac Myocytes from Hyperplasia to Hypertrophy During Postnatal Development, J Mol Cell Cardiol, 1996, 28:1737-1746.

Liao et al, Cardiac-specific overexpression of cyclin-dependent kinase 2 increases smaller mononuclear cardiomyocytes, Circ Res, 2001, 88:443-450.

Lu et al, Polymerizable Fab' antibody fragments for targeting of anticancer drugs, Nat Biotechnol, 1999, 17:1101-1104.

Malki et al, Clinical presentation, hospital lentgh of stay, and readmission rate in patients with heart failure with preserved and decreased left ventricular systolic function, Clin Cardiol, 2002, 25:149-152.

Mangi et al, Mesenchymal stem cells modified with Akt prevent remodeling and restore performance of infarcted hearts, Nat Med, 2003, 9:1195-1201.

Mastrobattista et al, Functional characterization of an endosome-disruptive peptide and its application in cytosolic delivery of immunoliposome-entrapped proteins, J Biol Chem, 2002, 277:27135-27143.

Matsuura et al, Adult cardiac Sca-1-positive cells differentiate into beating cardiomyocytes, J Biol Chem, 2004, 279:11384-11391.

Maxwell and Rivera, Proline oxidase induces apoptosis in tumor cells and its expression is frequently absent or reduced in renal carcinoma, J Biol Chem, 2003, 278:9784-9789.

Mbugua et al, Cardiotoxicity of Jamesoni's mamba (*Dendroaspis jamesoni*) venom and its fractionated components in primary cultures of rat myocardial cells in vitro, Cell Dev Biol, 1988, 24:743-752.

Mendez and Keys, Density and composition of mamalian muscle, Metabolism, 1960, 9:184-188.

Nagai et al, The Cell Cycle can be a New Target for the Treatment of Cardiac Hypertrophy?, J Mol Cell Cardiol, 1997, 33:1769-1771.

Neufeld et al, Coordination of Growth and Cell Division in the *Drosophila* Wing, Cell, 1998, 93:1183-1193.

Ng et al, An anti-transferrin receptor-avidin fusion protein exhibits both strong proapoptotic activity and the ability to deliver various molecules into cancer cells, PNAS, 2002, 99:10706-10711.

Nikolaev et al, Parc: a cytoplasmic anchor for p53, Cell, 2003, 112:29-40.

Oh et al, Cardiac provenitor cells from adult myocardium: homing, differentiation and fusion after infarction, PNAS, 2003, 100:12313-12318.

Oh et al, Telomerase reverse transcriptase promotes cardiac muscle cell proliferation, hypertrophy and survival, PNAS, 2001, 98:10308-10313.

Pagano et al, Cyclin A is required at two points in the human cell cycle, EMBO J, 1992, 11:961-971.

Parker and Schneider, Growth factors, proto-oncogenes, and plasticity of the cardiac phenotype, Annu Rev Physiol, 1991, 53:179-200.

Perin et al, Transendocardial, autologous bone marrow cell transplantation for severe, chronic ischemic heart failure, Circulation, 2003, 107:2294-2302.

Poolman et al, Altered Expression of Cell Cycle Proteins and Prolonged Duration of Cardiac Myocyte Hyperplasia in p27 KIP1 Knockout Mice, Circ Res, 1999, 85:117-127.

Beltrami et al, Evidence that human cardiac myocytes divide after myocardial infarction, N Engl J Med, 2001, 334:1750-1757.

Bianchi et al, Biochemical and structural evidence for pig myocardium adherens junction disruption by cardiopulmonary bypass, Circulation, 2001, 104:1319-1324.

Billy et al, Specific interference with gene expression induced by long, double-stranded RNA in mouse embryonal teracarcinoma cell lines, PNAS, 2001, 98:14428-14433.

Brooks et al, Arresting developments in the cardiac myocyte cell cycle: role of cyclin-dependent kinase inhibitors, Cardiovasc Res, 1998, 39:301-311.

Brooks et al, Expression and activities of cyclins and cyclin-dependent kinases in developing rat ventricular myocytes, J Mol Cell Cardiol, 1997, 29:2261-2271.

Casscells et al, Isolation, characterization, and localization of heparin-binding growth factors in the heart, J Clin Invest, 1990, 85:433-441.

Chatterjee et al, Viral gene transfer of the antiapoptotic factor Bcl-2 protects against chronic postischemic heart failure, Circulation, 2002, 106:1212-1217.

Chu et al, Toward highly efficient cell-type-specific gene transfer with retroviral vectors displaying single-chain antibodies, J Virol, 1997, 71:720-725.

Cottrell et al, Silence of the strands: RNA interference in eukaryotic pathogens, Trends Microbiol, 2003, 11:37-43 (abstract only).

Dorland's Medical Dictionary definition of heart failure.

Escobar et al, RNAi-mediated oncogene silencing confers resistance to crown gall tumorigenesis, PNAS, 2001, 98:13437-13442.

* cited by examiner

SIDE POPULATION CELLS IN CARDIAC REPAIR

CROSS-REFERENCE TO RELATED APPLICATIONS

This application claims priority from U.S. Provisional Application Ser. No. 60/720,765 filed on Sep. 26, 2005, which is incorporated herein by reference in its entirety.

INCORPORATION-BY-REFERENCE OF MATERIAL SUBMITTED ON A COMPACT DISC

Not Applicable.

STATEMENT REGARDING FEDERALLY SPONSORED RESEARCH OR DEVELOPMENT

This invention was made with government support under Grant No. K08 HL067048-03 awarded by National Institutes of Health. The government has certain rights in the invention.

FIELD OF THE INVENTION

The present invention generally relates to regeneration and repair of cardiac tissue.

BACKGROUND

It has been well established that adult mammalian cardiomyocytes lack significant replicative potential. Thus, myocyte loss in response to ischemic injury results in the formation of scar tissue and leads to insufficient cardiac function that is typically irreversible.

Recent evidence suggests that some cardiomyocytes in the diseased human heart have been found to re-enter the cell cycle in an attempt to compensate for the lost myocytes (Beltrami et al. (2001) N Engl J Med 344(23), 1750-1757). However, this process is thought to be inadequate in countering the massive myocyte loss seen after myocardial infarction. Thus, cell replacement strategies utilizing transplantation of exogenous cells have been studied. Bone marrow derived hematopoietic stem cells (BMCs) have been shown to exhibit the potential to differentiate into cardiomyocytes following transplantation (Jackson et al. (2001) J Clin Invest 107(11), 1395-1402, Orlic et al. (2001) Proc Natl Acad Sci USA 98, 10344-10349; Orlic et al. (2001) Nature 410(6829), 701-705). However, recent studies (Balsam et al. (2004) Nature 428(6983), 668-673; Murry et al. (2004) Nature 428 (6983), 664-668; Nygren et al. (2004) Nat Med 10(5), 494-501) have rigorously challenged the conclusions of these reports by independently demonstrating that BMCs transplanted into damaged hearts could not give rise to cardiomyocytes. Balsam et al. ((2004) Nature 428(6983), 668-673) have shown that not only do BMCs fail to give rise to cardiomyocytes, they actually develop into different blood cell types, despite being in the heart. The beneficial effects noted in earlier studies in terms of ventricular performance are thought to possibly be at least partially attributable to angioblast mediated vasculogenesis (Kocher et al. (2001) Nat Med 7)4) 430-436) which could prevent apoptosis of native cardiomyocytes rather than by direct myogenesis.

Side-population (SP) cells have stem cell characteristics as they have been shown to contribute to diverse lineages (see generally Challen and Little (2006) Stem Cells 24(1), 3-12). It has been found that SP cells can serve as progenitors for hematopoietic cells, skeletal muscle, and endothelium (see e.g., Asakura and Rudnicki (2002) Exp Hematol; Gussoni et al. (1999) Nature 401(6751), 390-394; Jackson et al. (2001) J Clin Invest 107(11), 1395-402). SP cells have been identified in the bone marrow as well as in nonhematopoietic tissues, including skeletal muscle, mammary gland, heart, liver, brain, kidney and lung (see e.g., Asakura, et al. (2002) J Cell Biol 159, 123-134; Welm et al. (2002) Dev Biol 245, 42-56; Martin et al. (2004) Dev Biol 265(1), 262-275; Summer et al. (2003) Am J Physiol Lung Cell Mol Physiol 285, L97-L104). SP cells have been identified in several species including mice, rhesus monkeys, swine and humans (SEE E.G., Goodell et al. (1997) Nat Med 3(12), 1337-1345; Storms et al. (2000) Blood 96(6), 2125-2133; Uchida et al. (2001) J Clin Invest 108(7), 1071-1077). In a recent study it was demonstrated that as few as 2000-5000 SP cells isolated from adult bone marrow were able to reconstitute the irradiated mdx mouse bone marrow (Gussoni et al. (1999) Nature 401(6751), 390-394). In another study, as few as 100 skeletal muscle SP cells were shown to reconstitute the entire bone marrow of a lethally irradiated mouse (Jackson et al. (1999) Proc Natl Acad Sci USA 96, 14482-14486). Another recent study demonstrated the adult heart contains SP cells capable of proliferation and differentiation, and that these cells are capable of participating in myocardial repair after cryoinjury is induced in the mouse heart Martin et al. (2004) Supplement to Circulation 110(17), 811).

Thus, there exists the need for therapeutic cell replacement strategies utilizing transplantation of autologous and/or exogenous cells for the treatment of heart disease.

SUMMARY

Disclosed herein is a new approach towards the regeneration and repair of cardiac myocytes utilizing SP cells. The disclosed compositions and methods can be used in various clinical applications.

One aspect of the invention is directed to a method for restoring cardiac function. In such methods an effective amount of a composition that includes side-population cells is introduced into the heart of a subject in need thereof. The side-population cells can be isolated side population cell. Aside from side population cells, the composition can also include various pharmaceutically acceptable carrier and/or adjuvants.

Generally, a subject upon which the methods of the invention are performed will have been diagnosed with myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy. Alternatively, it will have been determined that a subject upon which the methods of the invention are performed is at risk for myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy. Preferably, the subject will have been diagnosed with myocardial infarction or at risk for heart failure.

In various embodiments, the composition is implanted into the cardiac tissue of the subject. For example, implantation can be via injection delivery or catheter-delivery.

In various embodiments, the cardiac tissue into which the composition is introduced can be myocardium, endocardium, epicardium, connective tissue in the heart, or nervous tissue in the heart.

In various embodiments, the subject is an animal. Preferably, the subject is a mammal, more preferably a human.

In various embodiments, the side-population cells can be contacted with a cyclin-associated agent, so as to increase active levels of cyclin in the SP cells. Alternatively, heart tissue(s) can be can be contacted with a cyclin-associated agent, so as to increase active levels of cyclin in the heart tissue. It is also contemplated that a cyclin-associated agent, or several agents, can be used to increase active levels of cyclin in the SP cells and the heart tissue(s). Preferably, the cyclin-associated agent is a cyclin protein or a nucleic acid encoding a cyclin protein, more preferably a cyclin A2 protein or a nucleic acid encoding cyclin A2.

In various embodiments, side-population cell-containing composition is introduced in an amount sufficient to increase cardiomyocyte formation, increase cariomyocyte proliferation, increase cardiomyocyte cell cycle activation, increase mitotic index of cardiomyocytes, increase myofilament density, increase borderzone wall thickness, or a combination thereof. The amount of introduced composition will generally contain about $1 \times 10^8$ to about $1 \times 10^2$ side population cells. For example, the introduced composition can contain about $1 \times 10^6$ to about $1 \times 10^5$ side population cells.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

FIG. 1A shows an image of ejection fraction determined at each timepoint using functional MR imaging scans of heart tissue with a sagittal section and three perpendicular transverse sections over an ECG-gated cardiac cycle. FIG. 1B is a series of histograms showing ejection fraction percentages at 3 weeks and 3 months post-MI. There is a significant difference between transgenic and littermate controls at 3 weeks (p=0.045), and at 3 months (p=0.002). FIG. 1C is a series of histograms showing end diastolic volume (EDV) and end systolic volume (ESV) at 3 weeks and 3 months. There is a significant difference between groups for both EDV and ESV at both timepoints (p<0.05). FIG. 1D is a series of histograms showing ejection fraction for transgenic mice and littermate controls. There is no significant difference in EF between transgenic and littermate controls at 1 week post-MI. Further details regarding methodology are presented in Example 1.

FIG. 2A is an image of the peri-infarct zone. FIG. 2B is an image of the infarct zone. FIG. 2C is an image of normal rabbit serum used as the primary in place of H3P to demonstrate absence of nonspecific nuclear staining. Further details regarding methodology are presented in Example 3.

FIGS. 3A, 3B, and 3C are confocal microscopy images showing the presence of membrane ABCG2 localization (depicted by red signal) in "de novo" cardiomyocytes (depicted by the green fluorescence signal for αSA). FIG. 3D and FIG. 3E show cytoplasmic ABCG2 localization. FIG. 3F is a bright field microscopy image in which ABCG2 expression was confirmed by DAB immunohistochemistry, which verified that non-specific autofluorescent signals were not being detected. Further details regarding methodology are presented in Example 4.

FIG. 4A depicts co-immunofluorescence of cyclin A2 and αSA. FIG. 4B depicts the same section as in FIG. 4A with co-immunofluorescence of DAPI and αSA. Red=cyclin A2, Green=αSA, Blue=DAPI staining of nuclei. Further details regarding methodology are presented in Example 5.

FIG. 5A depicts cardiomyocytes dispersed from PN2 transgenic hearts. FIG. 5B depicts cardiomyocytes dispersed from nontransgenic hearts. No H3P staining was apparent in this figure. Blue=DAPI staining of nuclei, Green=αSA, Red=H3P. Both figures depict merged images of all three signals. FIG. 5C depicts the blue signal individually. FIG. 5D depicts the green signal individually. FIG. 5E depicts the red signal individually. FIG. 5F depicts the merged image of red, green, and blue signals, representing a PN2 transgenic cardiomyocyte undergoing cytokinesis with visualization of the contractile ring. FIG. 5G depicts a PN7 transgenic cardiomyocyte undergoing mitosis, with blue signal shown. FIG. 5H depicts a PN7 transgenic cardiomyocyte undergoing mitosis, with green signal shown. FIG. 5I depicts a PN7 transgenic cardiomyocyte undergoing mitosis, with red signal shown. FIG. 5H depicts a PN7 transgenic cardiomyocyte undergoing mitosis, with red, green, and blue signals merged. Further details regarding methodology are presented in Example 6.

DETAILED DESCRIPTION OF THE INVENTION

Figure 1:
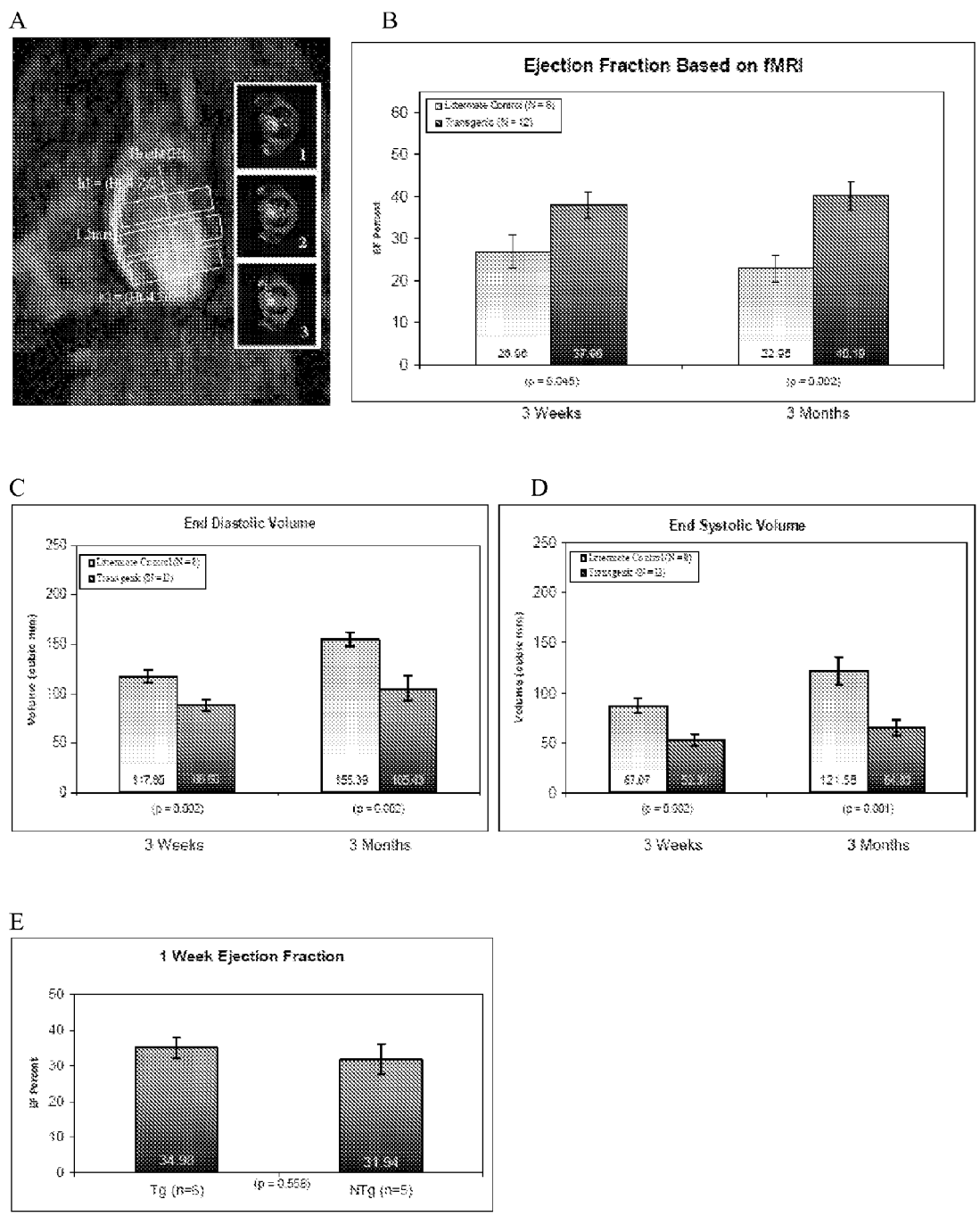
FIG. 1 is an image of a functional MR scan of heart tissue and a series of histograms depicting function of hearts post-infarction.

The approaches described herein are based at least in part upon application of the discovery of an increase in the frequency of SP cells in human patients with heart failure whose hearts exhibit signs of regenerative ability. Thus is provided a novel cellular therapy for tissue repair. Such therapeutic tissue repair utilizes SP cells, which are easily isolated and can be transplanted in an autologous manner. Methods and compositions described herein can be directed to, for example, cardiac repair, neural repair, hepatic repair, wound repair, lung repair, and renal repair. Preferably, the compositions and methods described herein are directed to cardiac repair.

Demonstrated herein is SP cells transplanted into the peri-infarct zone of infarcted mouse hearts can induce myocardial repair, prevent heart failure, and induce cardiac remodeling. It is also demonstrated herein that induced mitosis in cardiac progenitor cells, e.g., SP cells, in the infarct zone, peri-infarct zone, and distal myocardium can result in cardiac repair after MI. Furthermore, it is shown that the targeted expression cyclin A2, a mediator of cardiomyocyte mitosis, can augment endogenous regenerative processes by inducing cell cycle reentry of peri-infarct myocardium and repopulation of SP cell and/or SP cell derived cardiac progenitors in the infarct zone.

The methods of the invention generally involve intramyocardial transplantation of SP cells. Such therapeutic methods can repair and regenerate damaged myocardium and restore cardiac function after, for example, acute myocardial infarction and/or other ischemic or reperfusion related injuries. Methods generally include contacting a composition containing SP cells with cardiac tissue or cells.

In accordance with one method, a composition containing SP cells is introduced into the cardiac tissue or cells a subject. In brief, this method can be performed as follows. SP cells can be isolated by a variety of means known to the art. Once isolated, the side-population cells can be purified and/or expanded. The isolated SP cells can then be formulated as a composition comprising the SP cells along with, for example, a pharmaceutically acceptable carrier or adjuvant. The composition so formed can then be introduced into the heart tissue of a subject. The subject will usually have been diagnosed as having, or being at risk for, a heart condition, disease, or disorder. Introduction of the composition can be according to methods generally known to the art. For example, the SP cell composition can be administered to a subject's heart by way of direct injection delivery or catheter delivery. Introduction of SP cells can be a single occurrence or can occur sequentially over a period of time selected by the attending physician. The time course and number of occurences of SP cell implantation into a subject's heart can be dictated by monitoring generation and/or regeneration of cardiac tissue, where such methods of assessment and devisement of treatment course is within the skill of the art of an attending physician.

Cardiac tissue into which SP cells can be introduced includes, but is not limited to, the myocardium of the heart (including cardiac muscle fibers, connective tissue (endomysium), nerve fibers, capillaries, and lymphatics); the endocardium of the heart (including endothelium, connective tissue, and fat cells); the epicardium of the heart (including fibroelastic connective tissue, blood vessels, lymphatics, nerve fibers, fat tissue, and a mesothelial membrane consisting of squamous epithelial cells); and any additional connective tissue (including the pericardium), blood vessels, lymphatics, fat cells, progenitor cells (e.g., side-population progenitor cells), and nervous tissue found in the heart. Cardiac muscle fibers are composed of chains of contiguous heart-muscle cells, or "cardiomyocytes", joined end to end at intercalated disks. These disks possess two kinds of cell junctions: expanded desmosomes extending along their transverse portions, and gap junctions, the largest of which lie along their longitudinal portions. Each of the above tissues can be selected as a target site for introduction of SP cells, either individually or in combination with other tissues.

A determination of the need for treatment will typically be assessed by a history and physical exam consistent with the myocardial defect, disoder, or injury at issue. Subjects with an identified need of therapy include those with diagnosed damaged or degenerated heart tissue (i.e., heart tissue which exhibits a pathological condition). Causes of heart tissue damage and/or degeneration include, but are not limited to, chronic heart damage, chronic heart failure, damage resulting from injury or trauma, damage resulting from a cardiotoxin, damage from radiation or oxidative free radicals, damage resulting from decreased blood flow, and myocardial infarction (such as a heart attack). Preferably, a subject in need of treatment according to the methods described herein will be diagnosed with degenerated heart tissue resulting from a myocardial infarction or heart failure. The subject is preferably an animal, including, but not limited to, mammals, reptiles, and avians, more preferably horses, cows, dogs, cats, sheep, pigs, and chickens, and most preferably human.

It should be recognized that methods of this invention can easily be practiced in conjunction with existing myocardial therapies to effectively treat or prevent disease. The methods, compositions, and devices of the invention can include concurrent or sequential treatment with non-biologic and/or biologic drugs.

The subject receiving cardiac implantation of SP cells according to the methods described herein will usually have been diagnosed as having, or being at risk for, a heart condition, disease, or disorder. The methods of the invention can be useful to alleviate the symptoms of a variety of disorders, such as disorders associated with aberrant cell/tissue damage, ischemic disorders, and reperfusion related disorders. For example, the methods are useful in alleviating a symptom of myocardial infarction, chronic coronary ischemia, arteriosclerosis, congestive heart failure, dilated cardiomyopathy, restenosis, coronary artery disease, heart failure, arrhythmia, angina, atherosclerosis, hypertension, or myocardial hypertrophy. The condition, disease, or disorder can be diagnosed and/or monitored, typically by a physician using standard methodologies. Alleviation of one or more symptoms of the condition, disease, or disorder indicates that the composition confers a clinical benefit, such as a reduction in one or more of the following symptoms: shortness of breath, fluid retention, headaches, dizzy spells, chest pain, left shoulder or arm pain, and ventricular dysfunction.

Cardiac cell/tissue damage is characterized by a loss of one or more cellular functions characteristic of the cardiac cell type which can lead to eventual cell death. For example, cell damage to a cardiomyocyte results in the loss of contractile function of the cell resulting in a loss of ventricular function of the heart tissue. An ischemic or reperfusion related injury results in tissue necrosis and scar formation. Injured myocardial tissue is defined for example by necrosis, scarring, or yellow softening of the myocardial tissue. Injured myocardial tissue leads to one or more of several mechanical complications of the heart, such as ventricular dysfunction, decreased forward cardiac output, as well as inflammation of the lining around the heart (i.e., pericarditis). Accordingly, regenerating injured myocardial tissue according to the methdods described herein can result in histological and functional restoration of the tissue.

The methods of the invention can promote generation and/or regeneration of heart tissue, and/or promote endogenous myocardial regeneration of heart tissue in a subject. Promoting generation of heart tissue generally includes activating, enhancing, facilitating, increasing, inducing, initiating, or stimulating the growth and/or proliferation of heart tissue, as well as activating, enhancing, facilitating, increasing, inducing, initiating, or stimulating the differentiation, growth, and/or proliferation of heart tissue cells. Thus, the term includes initiation of heart tissue generation, as well as facilitation or enhancement of heart tissue generation already in progress.

Differentiation is generally understood as the cellular process by which cells become structurally and functionally specialized during development. Proliferation and growth, as used herein, generally refer to an increase in mass, volume, and/or thickness of heart tissue, as well as an increase in diameter, mass, or number of heart tissue cells. The term generation is understood to include the generation of new heart tissue and the regeneration of heart tissue where heart tissue previously existed.

Generation of new heart tissue and regeneration of heart tissue, resultant from the therapeutic methods described herein, can be measured or detected by procedures known to the art. Such procedures include, but are not limited to, Western blotting for heart-specific proteins, electron microscopy in conjunction with morphometry, simple assays to measure rate of cell proliferation (including trypan blue staining, the CellTiter-Blue cell viability assay from Promega (Madison, Wis.), the MTT cell proliferation assay from ATCC, differential staining with fluorescein diacetate and ethidium bromide/propidium iodide, estimation of ATP levels, flow-cytometry assays, etc.), and any of the methods, molecular procedures, and assays disclosed herein.

SP cells can be isolated, purified, and cultured by a variety of means known to the art (see e.g., Challen and Little (2006) Stem Cells 24(1), 3-12; Example 6). SP cells have a unique ability to extrude fluorescent vital dye Hoechst 33342, which is readily taken up by live cells where it binds to DNA (see e.g., Goodell et al. (1996) J Exp Med 183, 1797-1806). Analysis of these cells on a flow cytometer equipped with an ultraviolet (UV) laser source permits detection of these cells. For example, when unpurified murine bone marrow cells labeled with Hoechst are examined by fluorescence-activated cell sorter (FACS) analysis, SP cells fall within a separate population to the side of the remaining cells on a dot plot of emission data, hence the term "side population". Furthermore, methods of isolating, culturing, and differentiating stems cells are generally known in the art (see e.g., Lanza et al., eds. (2004) Handbook of Stem Cells, Academic Press, ISBN 0124366430; Lanza et al., eds. (2005) Essentials of Stem Cell Biology, Academic Press, ISBN 0120884429; Saltzman (2004) Tissue Engineering: Engineering Principles for the Design of Replacement Organs and Tissues, Oxford ISBN 019514130X; Vunjak-Novakovic and Freshney, eds. (2006) Culture of Cells for Tissue Engineering, Wiley-Liss, ISBN 0471629359; Minuth et al. (2005) Tissue Engineering: From Cell Biology to Artificial Organs, John Wiley & Sons, ISBN 3527311866). Such methods can be utilized directly or adapted for use with the SP cells.

As will be appreciated by one skilled in the art, the time between isolation, culture, expansion, and/or implantation can vary according to particular application. Incubation (and subsequent replication and/or differentiation) of the engineered composition containing SP cells can be, for example, at least in part in vitro, substantially in vitro, at least in part in vivo, or substantially in vivo. Determination of optimal culture time is within the skill of the art.

The SP cells can be derived from the same or different species as the transplant recipient. For example, the progenitor cells can be derived from an animal, including, but not limited to, mammals, reptiles, and avians, more preferably horses, cows, dogs, cats, sheep, pigs, and chickens, and most preferably human. It is also contemplated that autologous SP cells can be obtained from the subject, into which the SP cells are reintroduced. Such autologous SP cells can be expanded and/or transformed, as described herein, before re-introduction to the host.

SP cells can be obtained by screening a plurality of cells from donors. The population of cells to be screened are, preferably, those of heart tissue, and more preferably, those of heart tissue relatively rich in SP cells. But side-population cells can be obtained from any tissue known to contain such cells (see generally Challen and Little (2006) Stem Cells 24(1), 3-12). As a non-limiting example, SP cells can also be obtained from bone marrow. After screening, SP cells can be selected and prepared for transplantation.

If desired, the therapeutic SP cells can be expanded ex vivo (or in vitro) using, for example, standard methods used to culture SP cells and/or stem cells and maintain stable cell lines. Alternatively, these cells can be expanded in vivo (ie., after implantation). These cells can also be used for future transplantation procedures. The group of screened and isolated cells can, optionally, be further enriched for SP cells prior to transplantation. Methods to select for stem cells, for example SP cells, are well known in the art (e.g., MoFlow Cell Sorter). For example, samples can be enriched by tagging cell-surface markers of undifferentiated SP cells with fluorescently labeled monoclonal antibodies and sorting via fluorescence-activated cell sorting (FACS). Alternatively, a sample of the SP cell-rich culture can be implanted without further enrichment.

Isolated SP cells can optionally be transformed with a heterologous nucleic acid so as to express a bioactive molecule or heterologous protein or to overexpress an endogenous protein. Transformation of stem cells, including SP cells, is within the skill of the art.

As an example, SP cells can be genetically modified to expresses a fluorescent protein marker (e.g., GFP, EGFP, BFP, CFP, YFP, RFP). Marker protein expression can be especially useful in implantation scenarios, as described herein, so as to monitor SP cell placement, retention, and replication in target tissue. As another example, SP cells can be transfected with genetic sequences that are capable of reducing or eliminating an immune response in the host (e.g., expression of cell surface antigens such as class I and class II histocompatibility antigens may be suppressed). This may allow the transplanted cells to have reduced chance of rejection by the host, especially where the cells were from a different subject.

It may be desirable to increase levels of endogenous cell cycle regulators in SP cells and/or introduce exogenous cell cycle regulators into SP cells. As shown herein, SP cells with increased levels of cyclin A2 have augmented and/or prolonged proliferative potential (see e.g., Example 5). The SP cells can be contacted with, or transformed to express or overexpress, a variety of cell cycle regulators so as to achieve similar results. Elevated levels active cell cycle regulator (e.g., a cyclin) in SP cells can be accomplished by, for example, contacting or transforming the SP cells with a cell cycle regulator protein, or a protein variant thereof, or a cell cycle regulator-associated agent. Cyclin proteins include, but are not necessarily limited to, cyclins A, B, C, D, and E. Preferably, the level of active cyclin A2 in the SP cell is elevated (see e.g., U.S. Pat. Pub. No. 2006/0160733; Example 1). Various transport agents and delivery systems can be employed so as to effect intracellular transport of the cyclin protein into SP cells (see e.g., Stayton et al. (2005) Orthod Craniofacial Res 8, 219-225). As another option, the endogenous cyclin gene can be unsilenced by a variety of means known to the art. Alternatively or additionally, the SP cells can be engineered so as to express elevated levels of cyclin protein, or a protein variant thereof, or a cyclin-associated agent. Preferably, SP are transformed so as to express cyclin A2 (see e.g., U.S. Patent Pub. No. 2006/0160733, specifically incorporated herein by reference in its entirety). Isolated SP cells can be transduced with, for example, a lentiviral vector, retroviral vector, adenoviral vector, adeno-associated viral vector, or other vector system, overexpressing the cyclin gene. Preferably, isolated SP cells are transduced with a lentiviral vector overexpressing the cyclin A2 gene.

A protein is understood to include a protein, protein domain, polypeptide, or peptide, and any fragment or variant thereof having protein function. A protein variant has similar biological activity and at least 60% sequence identity (e.g., at least 65%, 70%, 75%, 80%, 85%, 95%, 95%, 96%, 97%, 98%, or 99%) to the protein of interest. An cell cycle regulator-associated agent includes, for example, a protein, polypeptide, peptide, nucleic acid (including DNA, RNA, and an antisense oligonucleotide), antibody (monoclonal and polyclonal, preferably human or humanized), Fab fragment, F(ab')2 fragment, molecule, compound, antibiotic, drug, and any combinations thereof, and may be an agent reactive (i.e., affinity for, binds to, or is directed against) with the cell cycle regulator. A cyclin A2-associated agent includes, for example, a cyclin protein, including an exogenous cyclin protein; a cyclin nucleic acid (i, e., a nucleic acid encoding a cyclin); a member of a cyclin signal-transduction pathway (including upstream and downstream effectors and activators, in either protein or nucleic acid form); and a modulator (e.g., inhibitor, activator, antagonist, or agonist) of a member of the cyclin signaltransduction pathway or system (i.e., a modulator which affects the expression, activity, function, and/or effect of a member of the cyclin signal-transduction pathway), in either protein or nucleic acid form, including a modulator of cyclin expression.

Contact of SP cells with cyclin A2 can occur before, during, or after isolation and/or purification. Similarly, contact of SP cells with cyclin A2 can occur before, during, or after implantation into a subject. Proteins and protein analogues of cyclin A2, as well as other proteins useful to the invention, can be generated by synthesis of polypeptides in vitro, e.g., by chemical means, or in vitro translation of mRNA (see e.g., U.S. Patent App. No. 2006/0160733). For example, cyclin may be synthesized by methods commonly known to one skilled in the art (see e.g., Benoiton (2005) Chemistry of Peptide Synthesis, CRC, ISBN 1574444549; Goodman et al., eds. (2004) Synthesis Of Peptides And Peptidomimetics: Workbench Edition, Thieme Medical Pub, ISBN 1588903117).

SP cells can be cultured and/or implanted along with other progenitor cell types. For example, SP cells can be cultured and/or implanted along with other stem cells, such as mesenchymal stem cells. As another example, SP cells can be cultured and/or implanted along with cardiomyoctyes. Co-culturing SP cells can induce SP cells to differentiate into cardiomyocytes (Martin et al. (2004) Dev Biol 265(1), 262-275). By varying the relative ratio of side-population cells to cardiomyocyte cells in culture, one can modulate the time course of differentiation.

The composition for delivery of SP cells can further comprise a pharmaceutical carrier, preferably an aqueous carrier. A variety of aqueous carriers can be used, e.g., buffered saline and the like. These solutions are sterile and generally free of undesirable matter. These compositions can be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, albumin, anticoagulants such as CPD (citrate, phosphate, and dextrose), dextran, DMSO, combinations thereof, and the like. The concentration of active agent in these formulations can vary widely, and can be selected primarily based on fluid volumes, viscosities, body weight, and the like, in accordance with the particular mode of administration selected and the subject's needs.

The present invention provides methods for enhancing cardiac function in a subject in need thereof by introducing SP cells into the heart of a subject. SP cell compositions can be directly introduced into, or contacted with, cardiac tissue and/or cells. Introduction to the tissues or cells of a subject can occur ex vivo or in vivo. Preferably, compositions containing isolated SP cells are directly implanted into cardiac tissue of the subject, in vivo.

Therapeutic SP cells can be implanted into the subject using standard methods (see e.g., Orlic et al. (2001) Nature 410(6829) 701-705; Example 7). Implantation of a SP cell-containing composition is within the skill of the art. For example, SP cells, or compositions comprising SP cells, can be introduced via direct injection (e.g., intermyocardial, intercoronary) or catheter-based delivery (e.g., intermyocardial, intercoronary, coronary sinus) intercoronary catheter directly injected into heart tissue. Because heart tissue can survive by diffusive transport alone, insufficient transport of transplanted cells does not generally present a significant problem.

The SP cells can be transplanted along with a carrier material, such as collagen or fibrin glue or other scaffold materials. Such materials can improve cell retention and integration after implantation. Such materials and methods for employing them are known in the art (see e.g., Saltzman (2004) Tissue Engineering: Engineering Principles for the Design of Replacement Organs and Tissues, Oxford ISBN 019514130X; Vunjak-Novakovic and Freshney, eds. (2006) Culture of Cells for Tissue Engineering, Wiley-Liss, ISBN 0471629359; Minuth et al. (2005) Tissue Engineering: From Cell Biology to Artificial Organs, John Wiley & Sons, ISBN 3527311866).

The amount of SP cells introduced into the heart tissue of the subject can be that amount sufficient to improve cardiac function, increase cardiomyocyte formation, and/or increase mitotic index of cardiomyocytes. For example, an effective amount is sufficient to increase cardiomyocyte formation, increase cardiomyocyte proliferation, increase cardiomyocyte cell cycle activation, increased mitotic index of cardiomyocytes, increase myofilament density, increase borderzone wall thickness, or a combination thereof. Improving or enhancing cardiac function generally refers to improving, enhancing, augmenting, facilitating or increasing the performance, operation, or function of the heart and/or circulatory system of a subject. An improvement in cardiac function may be readily assessed and determined by the skilled artisan, based on known procedures, including but not necessarily limited to, measuring volumetric ejection fraction using MRI.

An effective amount of SP cells can be, for example, about $1 \times 10^8$ to about 100 cells. For example, about $1 \times 10^8$, about $1 \times 10^7$, about $1 \times 10^6$, about $1 \times 10^5$, about $1 \times 10^4$, about $1 \times 10^3$, about $1 \times 10^2$ SP cells can constitute an effective amount. Preferably, about $1 \times 10^6$ to about $1 \times 10^5$ SP cells are introduced. One advantage of the present methods is derived, at least in part, from the potency of SP cells, such characteristics allowing introduction of relatively fewer SP cells than would be required in similar procedures with other cell types.

The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration; the route of administration; the duration of the treatment; drugs used in combination or coincidental with the specific composition employed and like factors well known in the medical arts. If desired, the total desired effective amount may be divided into multiple doses for purposes of administration. Consequently, single dose compositions may contain such amounts or submultiples thereof to make up the daily dose. It will be understood, however, that the total dosage of the compositions of the present invention will be decided by the attending physician within the scope of sound medical judgment.

Introduction of the SP cell-containing compositions can occur as a single event or over a time course of treatment. For example, compositions can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

References Cited

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention. It shall be understood that any method described in an example may or may not have been actually performed, or any composition described in an example may or may not have been actually been formed, regardless of verb tense used.

Example 1

Continued Expression of Cyclin A2 in Cardiomyocytes Mediate Cardiac Repair

Myocardial infarction (MI) was induced in transgenic and nontransgenic mice via permanent ligation of the LAD so as to test whether continued expression of cyclin A2 in cardiomyocytes could mediate cardiac repair. It has previously been shown that cyclin A2 functions as a critical regulator of cardiomyocyte mitosis.

Surgical Procedures: Cyclin A2 transgenic mice (Chaudhry et al. (2004) J Biol Chem 279(34), 35858-35866) were maintained in a B6CBA background. Nontransgenic littermates were used as controls. At 8 weeks of age, mice underwent left anterior artery (LAD) ligation to induce anterolateral MI. This was performed in a blinded manner. Each mouse was anesthetized, intubated, and subsequently underwent thoracotomy with LAD ligation under a surgical microscope. 41 transgenic and 41 non-transgenic mice were infarcted with an overall 79% survival rate at 1 week post infarct and did not differ significantly between groups.

Immunofluorescence and Confocal Microscopy: The infarcted mice were given serial intraperitoneal bromodeoxyuridine (BrdU) injections weekly at a concentration of 100 ug BrdU/g mouse. To examine response to the induced MI in the different groups, mice were sacrificed at 1 week, 2 weeks, 3 weeks, and 3 months of age. Each mouse was anesthetized with avertin. 3M KCl was injected into the beating heart to induce diastolic arrest. Hearts were perfused with 1× phosphate buffered saline (PBS) and fat tissue was removed. The hearts were fixed in 4% paraformaldehyde overnight. The atria were removed under a dissecting microscope, then the ventricles were sectioned into serial 1 mm thick slices with the first slice at the level of ligation of the LAD, dehydrated through ethanol series, and embedded in paraffin.

Sequential transverse sections (5 um) were cut. Co-immunofluorescence staining (Chaudhry et al. (2004) J Biol Chem 279(34), 35858-35866) was performed utilizing anti-α-sarcomeric actin with FITC-tagged anti-mouse IgM to identify cardiomyocytes. Antiphosphorylated histone-3 (Wei et al. (1998) Proc Natl Acad Sci USA 95, 7480-7484), anti-BrdU, anti-cyclin A2 were used to localize indices of cellular proliferation to cardiomyocyte nuclei. Rhodamine conjugated anti-rabbit IgG was used as the secondary antibody against antiH3P and anti-cyclin A2. Rhodamine-tagged anti-rat IgG was the secondary to anti-BrdU. Anti-ABCG2 was used to identify SP cells with rhodamine-tagged anti-rabbit IgG as the secondary. Nuclei were stained with DAPI. All analyses were performed under 40× and 100× magnification using confocal microscopy. Immunohistochemistry with bright field microscopy (Chaudhry et al. (2004) J Biol Chem 279 (34), 35858-35866) was also performed on serial sections adjacent to sections analyzed by co-immunofluorescence for the localization of ABCG2 expression to cardiomyocytes to exclude non-specific auto fluorescence. Other preparative steps taken to obviate autofluorescence signals involved the use of Sudan Black to quench the autofluorescence of cardiomyocytes. After the end of the immunofluorescence staining protocol, slides were placed in a 0.1% solution of Sudan Black in 70% ETOH for 30 minutes.

Assessment of Cardiac Function: MRI image acquisition (performed by H. Tang in a blinded manner) was performed on a 9.4 Tesla Bruker WB400 microimaging system with 30 mm quadrature RF coil (Brucker NMR Inc., Bellerica, Mass.). The mice were anesthetized with isoflurane (1.5% volume in 2 L/min air flow). The heart rate was ~450 bpm. Quantitation of ventricles was based on bright blood 2D image stacks acquired using ECGgated fast gradient echo cine sequence. Magnetic resonance imaging (MRI) was performed at 3 weeks and 3 months post-MI. To measure volumetric EF, three transverse images were scanned at equal distances from the mid-point of the long axis of the heart, taken from a sagittal scan (FIG. 1A). Assuming that the volume of an ellipsoid=⅔Ah, where A=area, h=height, total volume=⅔A1h1+1.5A1+1.5A2+1.5A3+⅔A3h2. For each A (A1, A2, A3) left ventricular (LV) end-systolic area was subtracted from LV end-diastolic area to obtain volumetric EF.

Assessment of Infarction Size: To determine the extent of infarction, 5 μm serial paraffinembedded sections of the heart underwent Masson's trichrome staining. Imagetool (UTH-SCSA, Texas) was utilized to measure the circumference of infarcted ventricle in each section. Based on these measurements and the mass of each slice used to generate the section, the infarction percent was calculated for each heart.

Myocyte Dispersion and Assessment of Mitotic Index in Cultured Myocytes: Between 20-26 postnatal day (PN) 2 or PN7 pups were used to isolate cardiomyocytes. Hearts were minced, the tissue was placed in 2 ml of Hank's Buffer, 2 ml of Pronase (0.01 g/mL) was added and incubated at 37° C. for 30 minutes. The muscle cell suspension was pelleted and trituration of the tissue was performed in Dulbecco's Modified Eagle Medium (DMEM) containing 2% fetal bovine serum, 1% penicillin, 1% glutamine, 1% hepes and 20 $\propto$ g/ml gentamycin. It was filtered, pelleted and resuspended in 3 ml Hanks plus serum. It was pelleted again and resuspended in warm DMEM. Pre-plating with fibronectin solution (1 mg/40 ml DMEM) was utilized to minimize fibroblasts. After pre-plating, cells were counted. Approximately $4 \times 10_6$ cells per 2 ml of DMEM medium were transferred into LabTek II slide wells (Nalge Nunc International, Naperville, Ill.) and incubated overnight. Transgenic cardiomyocytes were plated separately from nontransgenic cardiomyocytes. The Petri dishes were exposed to 30 minutes of gamma irradiation (Gamma Cell 40 using Cs-137 isotope) the next day to minimize fibroblasts. DMEM was aspirated from the slide wells and fresh 2 ml DMEM added. Cells were cultured for 4-7 days.

The cells were fixed with 4% PFA and double immunofluorescence staining was performed as described above to identify mitotic nuclei and cardiomyocyte cytoplasm. Cells were analyzed using confocal microscopy (Zeiss LSM 510 NLO Multiphoton Confocal Microscope). A mitotic index was computed for transgenic and nontransgenic cells by computing the ratio of mitotic cardiomyocytes to total number of cardiomyocytes.

Data was expressed as mean±s.e.m. Student's t-test was used for data comparison, using a significance level of $p<0.05$.

Results showed that the percentage of infarcted LV volume was consistent between groups (transgenic: 46.8+3.6, non-transgenic: 49.5+4.3, p=0.64) indicating that the transgenic and nontransgenic groups were comparable at 1 week. Cardiac function was analyzed in a serial manner utilizing MRI to measure volumetric ejection fraction (EF). Volumetric EF was markedly enhanced in transgenic mice at 3 weeks post-MI (see e.g., FIG. 1B) and at 3 months post-MI. Left ventricular end-diastolic and end-systolic volume (EDV and ESV, respectively) were markedly decreased in transgenic mice at both time points, implying that the presence of cyclin A2 expression prevents the normal ventricular dilation process after MI (see e.g., FIG. 1C).

To define a time course for the enhancement of cardiac function noted in the transgenic mice, infarctions were induced in a second set of mice (6 transgenic and 5 nontransgenic). Results showed that volumetric EF did not significantly differ between the two groups at 1 week post-MI (see e.g., FIG. 1D).

Example 2

Post-Myocardial Infarction Cell Cycle Activity

To elucidate putative cellular and molecular mechanisms underlying the marked enhancement of cardiac function in transgenic mice, DNA synthesis was analyzed by sequential labeling with BrdU for 3 months post-MI to assess cell cycle activity (see e.g., Table 1). Five sections from each heart were analyzed at 1, 2, 3 weeks and 3 months postMI (n=3-5 per group at each time point). At 3 months, $2.95 \times 10^6$ cardiomyocytes/mouse (n=5) were scored for non-transgenics and $2.30 \times 10^6$ cardiomyocytes/mouse (n=5) for cyclin A2 transgenics.

Methods were as described in Example 1, except as otherwise noted.

Results showed that, for the non-transgenics, there was an average of 0.001% cardiomyocytes/mouse that co-stained for BrDU and αSA in the peri-infarct zone. For the cyclin A2 transgenics, there was an average of 0.48% cardiomyocytes/mouse costaining for BrDU and αSA in the peri-infarct zone. These results indicate that cell cycle reentry occurs in transgenic but not in nontransgenic myocardium in response to injury.

TABLE 1

% BRDU-positive Cardiomyocytes in the Left Ventricle and Distal Regions. Cardiomyocyte DNA synthesis is significantly increased in infarcted transgenic mice. Percent BrdU-positive cardiomyocytes noted in the peri-infarct (LV) and distal regions (RV) after sequential labeling for 3 months post-infarct.

| 3 months | LV | SEM | Distal | SEM |
|---|---|---|---|---|
| Tg (n = 5) | 0.478 | 0.137 | 0.115 | 0.053 |
| NTg (n = 5) | 0.001 | 0.000 | 0.000 | 0.000 |
| p-value | 0.01 | | 0.06 | |

Example 3

Cardiomyocyte Mitosis in Transgenic Infarcted Hearts

To assess the presence of mitotic cardiomyocyte nuclei, mitoses were detected utilizing anti-phosphohistone H3 antibody (H3P) (Wei (1998) Proc Natl Acad Sci USA 95, 7480-7484) and localized to cardiomyocytes by co-localization of α-sarcomeric actin (αSA).

Methods were as described in Example 1, except as otherwise noted. A mitotic index was generated for both transgenic and nontransgenic hearts as the ratio of cardiomyocyte mitoses to total cardiomyocyte nuclei (Chaudhry et al. (2004) J Biol Chem 279(34), 35858-35866). Mitotic indices were generated for the peri-infarct zone, which encompassed non-infarcted LV, and distal myocardium encompassing the right ventricle. In the infarct zone, an index could not be computed due to the low numbers of intact myocytes.

Mitotic indices for transgenic and nontransgenic hearts at 3 weeks and 3 months post-MI are shown in, for example, Table 2. Results showed that, prior to 2 weeks post-MI, cardiomyocyte mitoses were not detected in either group (data not shown). At 3 weeks, $2.65 \times 10^6$ cardiomyocytes/mouse (n=4) were scored for non-transgenics and $2.52 \times 10^6$ cardiomyocytes/mouse (n=4) for cyclin A2 transgenics. For the non transgenics, there was an average of 0.00% cardiomyocytes/mouse that co-stained for H3P and αSA in the peri-infarct zone. For the cyclin A2 transgenics, there was an average of 0.016% cardiomyocytes/mouse co-staining for H3P and αSA in the peri-infarct zone.

TABLE 2

Mitotic Indices (% H3P-positive Cardiomyocytes) in the Left Ventricle and Distal Regions. Cardiomyocyte mitotic indices are significantly enhanced in infarcted transgenic hearts. Percent of cardiomyocytes that are positive for phosphorylated histone H3 (H3P), a mitosisspecific marker, at 3 weeks and 3 months in the pen-infarct/left ventricle (LV) and distal infarct/right ventricle (RV) regions. Measurements were confirmed under confocal microscopy.

| 3 weeks | LV | SEM | Distal | SEM |
|---|---|---|---|---|
| Tg (n = 5) | 0.478 | 0.137 | 0.115 | 0.053 |
| NTg (n = 5) | 0.001 | 0.000 | 0.000 | 0.000 |
| p-value | 0.01 | | 0.06 | |
| Tg (n = 5) | 0.018 | 0.009 | 0.006 | 0.003 |
| NTg (n = 5) | 0.000 | 0.000 | 0.000 | 0.000 |
| p-value | 0.05 | | 0.10 | |

At 3 months, $2.95 \times 10^6$ cardiomyocytes/mouse (n=5) were scored for non-transgenics and $2.30 \times 10^6$ cardiomyocytes/mouse (n=4) for cyclin A2 transgenics. In terms of co-localization of H3P and αSA, there was an average of 0.00% cardiomyocytes/mouse in the non-transgenic peri-infarct zone. In the cyclin A2 transgenics, there was an average of 0.018% cardiomyocytes/mouse co-expressing H3P and αSA in the peri-infarct zone.

Figure 2:
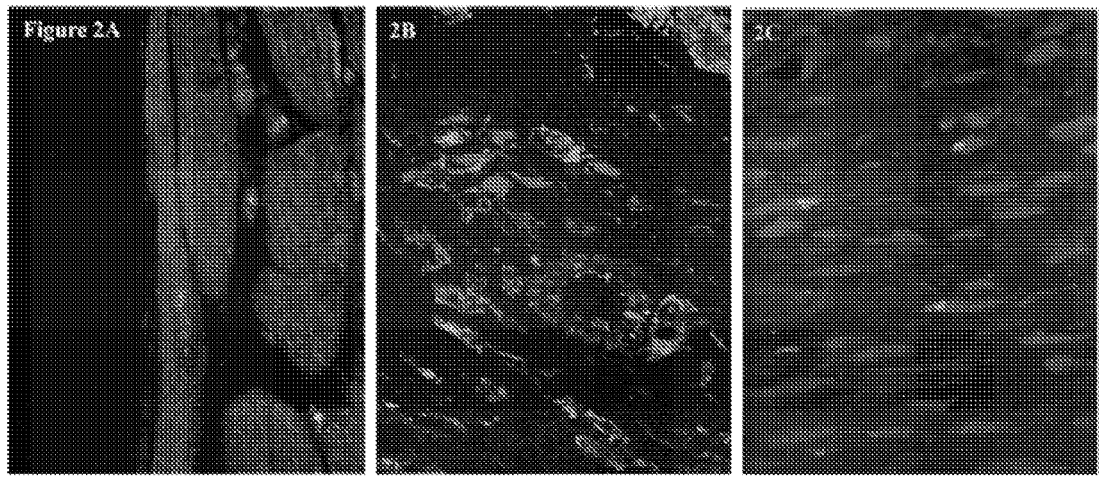
FIG. 2 is a series of images of transgenic infarcted heart tissue depicting cardiomyocyte mitoses. The presence of H3P (depicted by red signal) is highly specific for mitosis. Immunostaining for αSA (depicted by green signal) was utilized to identify mitotic nuclei (nuclei are depicted by blue DAPI signal) as cardiomyocytes.
Figure 3:
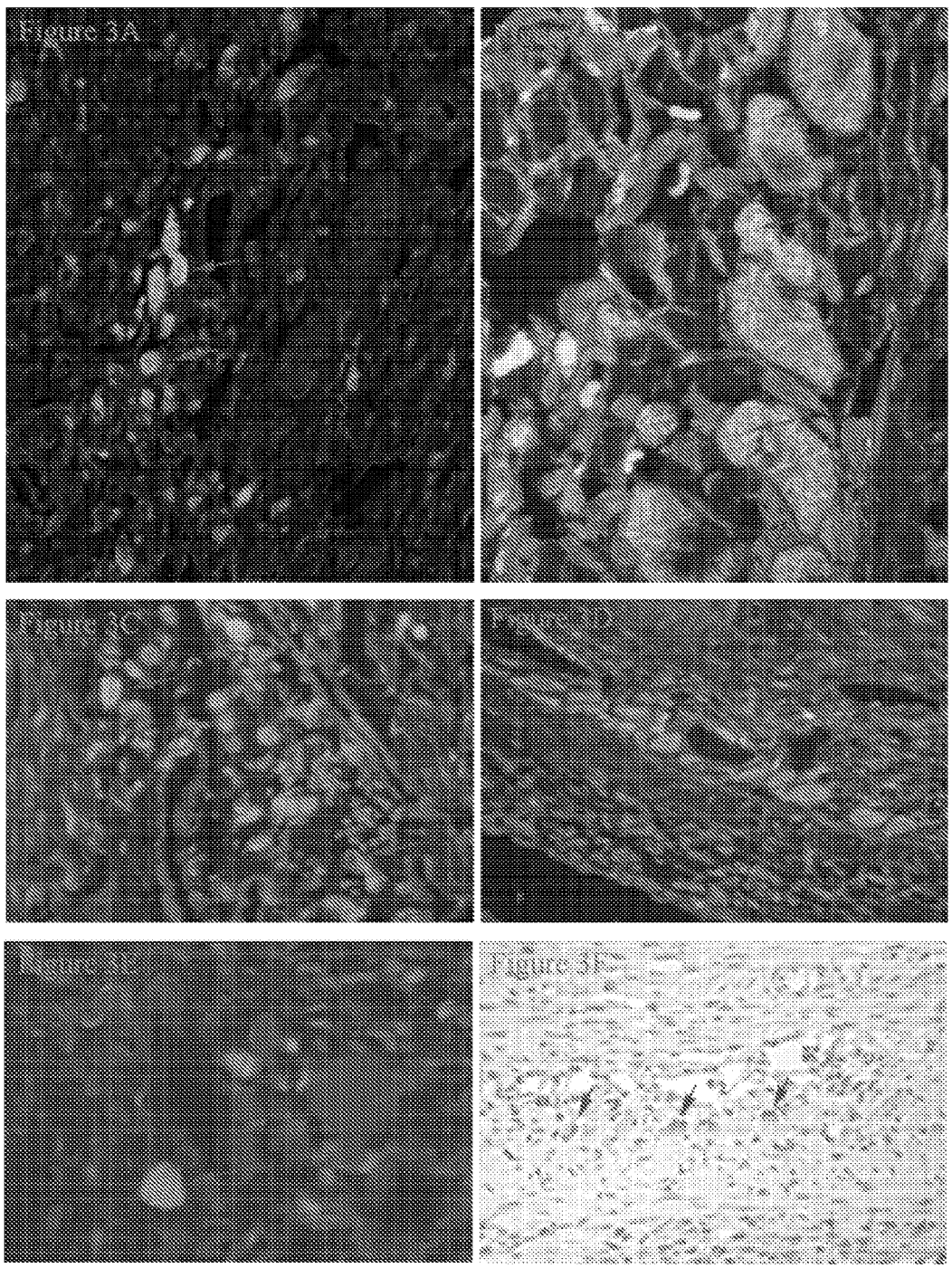
FIG. 3 is a series of images of heart tissue depicting ABCG2 expression as a Marker of SP cells. ABCG2 was found on putative cardiomyocyte progenitor cells in the infarcted hearts. ABCG2, a member of the ATP-cassette transporter family of proteins has been shown to be a marker of SP cells that can be found in the myocardium.

At both time points, a greater number of mitoses were noted in the peri-infarct zone compared with the distal zone of transgenic hearts. Conversely, no mitotic cardiomyocytes were noted in nontransgenic hearts at all time points. Confocal images of mitotic cardiomyocytes in the peri-infarct zone of transgenic hearts are shown in, for example, FIG. 2A.

Mitoses were also noted in the infarct zone in small, αSA-positive cells (~5 µm), that had a high nuclear to cytoplasmic ratio. Three mid-ventricular transverse sections from each infarcted zone of the non-transgenic hearts (n=5) and cyclin A2 transgenic hearts (n=5) were thoroughly examined under confocal microscopy at 3 weeks and 3 months. There were small cells co-expressing αSA and H3P identified in the infarct zone. At 3 weeks, there was an average of 0 cells/mouse co-expressing αSA and H3P in the nontransgenics, and an average of 3.4 cells/mouse co-expressing αSA and H3P in the transgenics. At 3 months, there was an average of 0.4 cells/mouse co-expressing αSA and H3P in the nontransgenics, and an average of 6.5 cells/mouse co-expressing αSA and H3P in the transgenics. They were not noted at 1 and 2 weeks post-MI in either group. Confocal images of these small cells that co-express H3P and αSA noted in the infarct zone of transgenic hearts are illustrated in, for example, FIG. 2B.

Thus is demonstrated that cyclin A2 is able to mediate cardiac repair by inducing mitoses in the infarct zone, peri-infarct zone, and distal myocardium after MI. The transgenic mice had markedly improved EF at 3 weeks and 3 months post-MI compared with nontransgenic mice, with significantly diminished ventricular remodeling. The lack of significant differences in EF between the groups at 1 week post-MI helps define a time-course for recovery. Mitoses were not noted prior to 2 weeks post MI.

Example 4

Characterization of Early Stage Cardiomyocytes in the Infarct Zone

The small cardiomyocyte cells (at early stages of differentiation, possessed of small size and high nuclear to cytoplasmic ratio,) that were noted in the infarct zone were further characterized. ABCG2, a member of the ATP-binding cassette transporter family of proteins, is well established as a marker of side-population cells (Zhou et al. (2001) Nat Proc Med 7, 1028-1034). These have been found in a variety of adult tissues and are thought to represent a class of pluripotent stem cells in which expression of ABCG2 diminishes as differentiation proceeds (Wei et al. (1998) Proc Natl Acad Sci USA 95, 7480-7484). ABCG2 has recently been shown to be expressed in cardiac progenitor cells, with the highest levels of expression in mice noted at embryonic day 8.5 (Martin et al. (2004) Dev Biol 265, 262-275).

Methods were as described in Example 1, except as otherwise noted. Confocal analysis was utilized to detect αSA and ABCG2 co-immunofluorescence.

Results showed that small cells that co-expressed both markers were noted in both transgenic and nontransgenic infarct zones at 2 weeks postMI but not at 1 week post-MI (see e.g., FIG. 3A-3F). They were noted to occur with equal frequency in transgenic and nontransgenic hearts; however, mitoses in these small cells were predominantly limited to transgenic hearts as described above. In some sections, the typical membrane-expression pattern of ABCG2 was noted (see e.g., FIG. 3A, B, C) whereas other sections exhibited a cytoplasmic location (see e.g., FIG. 3D, E, F). Bright field microscopy was used to identify ABCG2 expression as further confirmation of specific signal and to exclude non-specific auto-fluorescent signal (see e.g., FIG. 3F—a serial section adjacent to that pictured in 3D). An analysis of cKit expressing stem cells was performed in transgenic and non-transgenic hearts at 2 weeks post-MI (n=3 for each group). Clusters of cKit-positive cells with high nuclear to cytoplasmic ratio were seen occurring at equal frequency in both transgenic and nontransgenic infarct zones (data not shown).

The observation of small cells co-expressing αSA and ABCG2 was representative of cardiac progenitors in the infarct zones of both transgenic and nontransgenic hearts. The significantly enhanced mitotic indices and parameters of cardiac function noted in transgenic hearts was indicative of increased cycling of cardiac progenitors in transgenic mice.

Thus is demonstrated that enhanced mitotic activity of cardiac progenitors cells, specifically SP cells, can induce cardiac repair post-MI.

Example 5

Cyclin A2 Expression Associated with Enhanced Cycling of Cardiomyocytes

Cyclin A2 expression was assessed in both transgenic and nontransgenic hearts at 2 weeks post-MI. As previously determined, nuclear localization of cyclin A2 is associated with cardiomyocyte mitosis (Chaudhry et al. (2004) J Biol Chem 279(34), 35858-35866). Nuclear expression of the cyclin A2 transgene protein product is only detected in early postnatal development, and by 2 weeks of age, it is localized mainly in the cytoplasm of transgenic hearts (cyclin A2 is not detectable after postnatal day 2 in nontransgenic in either location).

Methods were as described in Example 1, except as otherwise noted.

Figure 4:
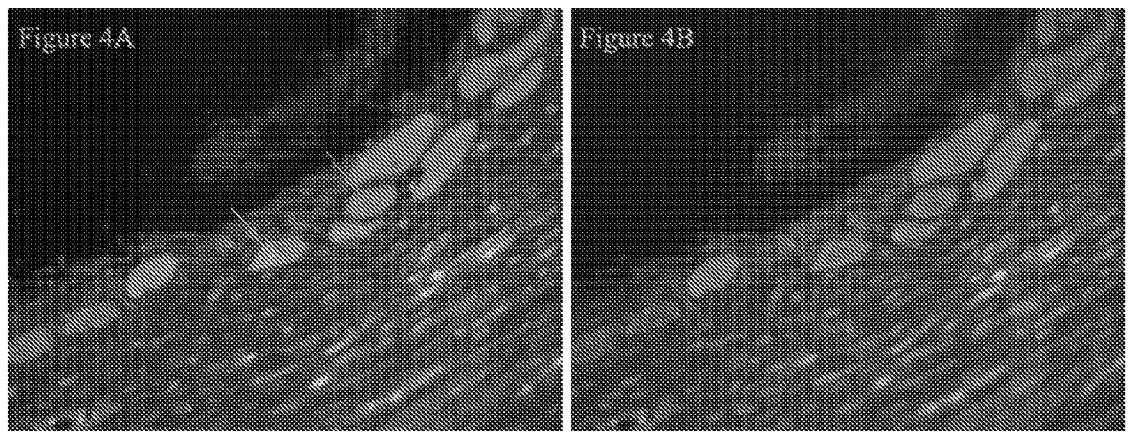
FIG. 4 is a series of images of heart tissue depicting cyclin A2 expression localization in nuclei of "de novo" myocytes of infarcted transgenic hearts.

Results showed that cyclin A2 protein was detected in transgenic infarct zone cardiomyocyte nuclei, but not in non-transgenic infarct zones (see e.g., FIG. 4A, B). As the mice underwent infarction at 8 weeks of age, they were 10 weeks old at the time of this analysis. As the mice were 10 weeks of age for this analysis, and transgenic mice do not exhibit nuclear expression of cyclin A2 beyond 2 weeks of age (18), these cardiomyocytes are thought to represent immature cardiomyocytes.

These results indicate that cardiomyocytes derived from ABCG2 expressing progenitors in the infarcted myocardium recapitulate the developmental paradigm noted in the early postnatal cyclin A2 transgenic hearts (Chaudhry et al. (2004) J Biol Chem 279(34), 35858-35866); that is, mitosis is potentiated in postnatal cardiomyocytes expressing cyclin A2. It is thought that cyclin A2 is directing increased rounds of mitosis of the "immature" cardiomyocytes in the infarct zones of the transgenic mouse hearts. Additionally, the cell cycle re-entry of peri-infarct myocardium indicates a retention of perhaps a more "plastic" phenotype in the transgenic heart.

Thus is demonstrated that induction of cardiac repair post-MI by enhanced mitotic activity of cardiac progenitors cells, such as SP cells, is associated with cyclin A2 in the nuclei of cardiac progenitors.

Example 6

Proliferative Potential of Ex Vivo Transgenic Cardiomyocytes

To examine the enhanced proliferative potential of the transgenic cardiomyocytes, cells were isolated from PN2 and PN7 transgenic and nontransgenic mice and cultured for 4-7 days, and examined for mitotic activity by staining with anti-αSA and anti-H3P. Cells at this stage of development were chosen for this analysis as they should closely mimic the immature cardiomyocytes noted in the infarct zones of the adult mouse hearts. Methods were as described in Example 1, except as otherwise noted.

Figure 5:
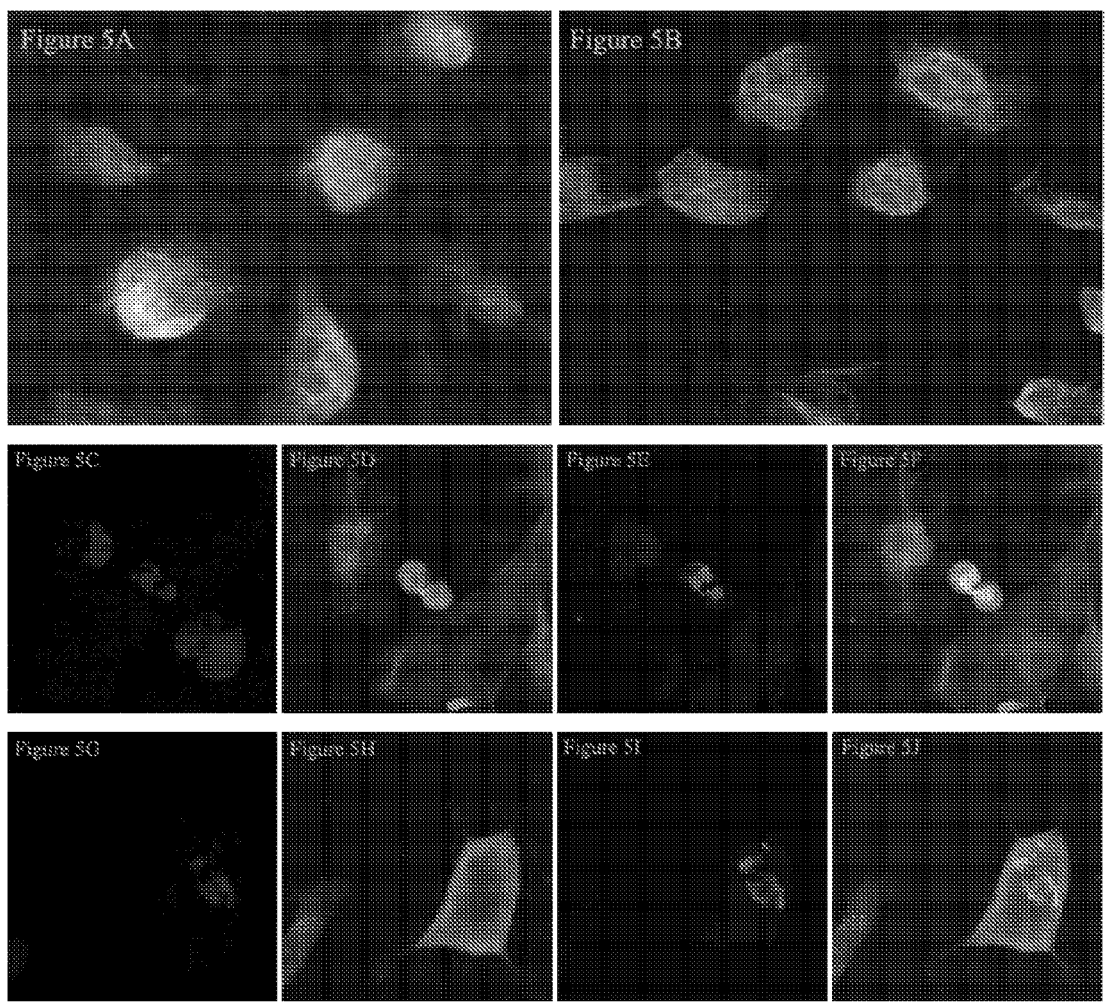
FIG. 5 is a series of images of heart tissue depicting cyclin A2 expression and proliferation of postnatal cardiomyocytes in culture.

Results showed that a significantly enhanced mitotic index was noted in the PN2 transgenic cardiomyocytes compared with nontransgenic (0.089+0.010 vs. 0.014+0.008, $p<0.0001$) (see e.g., FIG. 5A, B). Several cells from transgenic hearts were undergoing cytokinesis (see e.g., FIG. 5C,D,E,F) whereas this was not noted in the cells from nontransgenic hearts. At PN7, occasional mitoses were noted among the cultured transgenic cells (see e.g., FIG. 5G,H,I,J) but no mitoses were noted in the nontransgenic cells.

Thus it is demonstrated that postnatal (immature) transgenic cardiomyoctes (e.g., SP cells) in culture exhibit a significantly higher mitotic index than nontransgenic cells and can undergo cytokinesis, thus reinforcing the role of SP cells and cyclin A2 in cardiac repair.

Example 7

Transplant of SP Cells Into Peri-Infarct Zone

Myocardial infarction is induced via ligation of the left anterior descending artery (LAD) followed by transplant of SP cells from either GFP+CycA2+ or GFP+CycA2− mice into the peri-infarct zone. Cardiac function and parameters of cell proliferation are then followed.

Four to five month-old male GFP+CycA2+ mice, generated on a B6CBA background and their GFP+CycA2− male littermates are used as bone marrow donors. Wild type female B6CBA mice, age 3 months, are used as recipients. Recipients are divided into 3 groups. Each group includes 15-20 mice. Group 1 receives SP cells derived from GFP+CycA2− mice. Group 2 receives SP cells derived from GFP+CycA2+ mice. Group 3 receives GFP+ mouse fibroblasts. Group 4 serves as an additional control and receives an equal volume of phosphate buffered saline (PBS). Group 5 is sham infarcted and receives no treatment. All experiments were blinded experiments.

Side-population cells are isolated as described above. Generally, yield is about 200,000 SP cells/6 mice. Cells are analyzed and sorted for the Hoechst-low SP phenotype using the M (DakoCytomation, Carpinteria, Calif.). Fluorescence is measured at two oFlo cell sorting system wavelengths using filters for blue (407 nm) and red (670 nm) emission. A live gate is defined on the flow cytometer using Hoechst red and blue axes to exclude dead cells, red cells, and debris. Verapamil inhibition is used to verify the correct population has been sorted. Sorted SP cells arew collected for transplantation.

Recipient WT female mice in each group undergo LAD ligation to induce anterolateral myocardial infarction. As performed, LAD ligation survival rate is 79% at 1 week post-infarction with highly reproducible infarction volumes. Each mouse will be anesthetized, intubated and undergo thoracotomy with LAD ligation under a surgical microscope.

To determine if SP cells can function as authentic cardiac progenitors in vivo in the post-infarct heart, intramyocardial (see e.g., Orlic et al. (2001) Nature 410(6829) 701-705) SP cell transplantation is performed. 3 days after LAD ligation (allowing for the post-infarct inflammatory response to subside) SP cells ($1 \times 10^5$) will be injected into the peri-infarct border zone of the left ventricle in mice belonging to group 1 and 2. Mouse fibroblasts will be injected into the hearts of group 3. Mice in group 4 will receive an equal volume of PBS.

Immunohistochemistry is performed to assess the fate of transplanted SP cells in the recipient's myocardium. All the infarcted mice are given serial intraperitoneal bromodeoxyuridine (BrdU) injections weekly at a concentration of 100 μg/g mouse. BrdU labeling measures cell proliferation by quantitating BrdU incorporated into the newly synthesized DNA of replicating cells. Three weeks post SP cell transplantation, 5 mice each from groups 1, 2 and 3 are sacrificed. Each mouse is anesthetized with avertin. 3M KCL solution is injected into the beating heart to induce diastolic arrest. Fat tissue and atria is removed. Hearts are perfused with 1× phosphate buffered saline (PBS) and fixed in 4% paraformaldehyde overnight. The ventricles are sectioned into serial 1 mm thick slices with the first slice at the level of the ligation of LAD, dehydrated through ethanol series and embedded in paraffin. Sequential transverse section (5 um) are cut. Co-immunofluorescence staining is performed to detect mitoses. Antibody against alpha-sarcomeric actin is used to identify cardiomyocyte cytoplasm. Antibody to phosphorylated histone-3 (H3P), a marker highly specific for mitosis, is used to detect mitotic nuclei. Anti-BrdU antibody is used to detect DNA synthesis in the cells. AntiABCG2 antibody is used to detect the expression of ABCG2 in the cardiac progenitor cells. Antibody to cyclin A2 is used to detect the expression of cyclin A2. Analysis is performed under 40× and 100× magnification using confocal microscopy. The number of cardiomyocyte nuclei staining positively for H3P is counted per field at 40× magnification under fluorescent field optics. The total number of cardiomyocyte nuclei per field is counted, and a mitotic index computed as the ratio of H3P-positive nuclei to total nuclei.

To identify donor derived male SP cells in the myocardium of WT female recipients, GFP expression is utilized to track donor cells. Fluorescence in situ hybridization (FISH) is performed (see e.g., Orlic (2001) Nature 410(6829), 701-705) as an additional method to track the donor cells. At 3 weeks post SP cell transplantation, fixed tissue sections from 5 mice each in group 1 group and group 2 are analyzed for the presence of donor male nuclei by Y chromosome specific FISH analysis. Whole chromosome paint probes (Cambio, UK) are used to image the Y chromosome in the recipient myocardium. The hybridization of the probe with the cellular DNA site is visualized by fluorescence microscopy using a probe labeled with a fluorophore. Using the paraffin pretreatment kit (Vysis, Ill.), paraffin embedded tissue sections are deparaffinized and pretreated to maximize tissue permeability and hybridization. After denaturation of the sample DNA, probe is applied to the slides for hybridization to occur. After hybridization unbound probe is removed via a rapid wash procedure. DAPI is used to counterstain the nuclei.

To determine the extent of infarction, 5 um serial paraffin embedded sections of the heart from mice in groups 1, 2 and 3 undergo Masson's trichome staining. Imagetool (UTH-SCSA, Texas) is utilized to measure the circumference of infarcted relative to noninfarcted left ventricle in each section. Based on the measurements and the mass of each slice used to generate the section, the infarction percent is calculated for each heart.

To address the potential beneficial effects of SP cells on ventricular function after myocardial infarction, magnetic resonance imaging (MRI) is conducted. MRI analysis is the most technologically advanced modality for assessing cardiac mass and function, and is the most accurate and reliable method for noninvasively quantifying left ventricular mass and function in mice (Wiesman (2000) Am J Physiol Heart Circ Physiol 278(2), H562-657). At 3 weeks and again at 3 months post SP cell transplantation, 15 WT female mice each in groups 1, 2, 3, and 4 undergo functional magnetic resonance imaging (MRI) for determination of cardiac function. MRI image acquisition is performed on a 9.4 Tesla Bruker WB400 microimaging system with 30 mm quadrate RF coil (Brucker NMR Inc, Bellerica, Mass.). The mice are anesthetized with isoflurane. Quantitation of the ventricles is based on bright blood 2D image stacks acquired using ECG-gated fast gradient echo cine sequence. To measure volumetric EF, three transverse images are scanned at equal distances from the midpoint of the long axis of the heart, taken from a sagittal scan. Assuming that the volume of an ellipsoid=⅔Ah (A=area, h=height), total volume=⅔A1h1+1.5A1+1.5A2+1.5A3+⅔A3h2. For each A (A1, A2, A3) left ventricular (LV) end systolic area is subtracted from LV end diastolic area to obtain volumetric EF.

Example 8

SP Cell Transplant Restores Cardiac Function After MI

Cardiac function was assessed after SP cells (either GFP+ CycA2+ or GFP+CycA2−) were transplanted into the peri-infarct zone mice with ligation-induced myocardial infarction. Methodology was as described in Example 7, except where otherwise noted.

Figure 6:
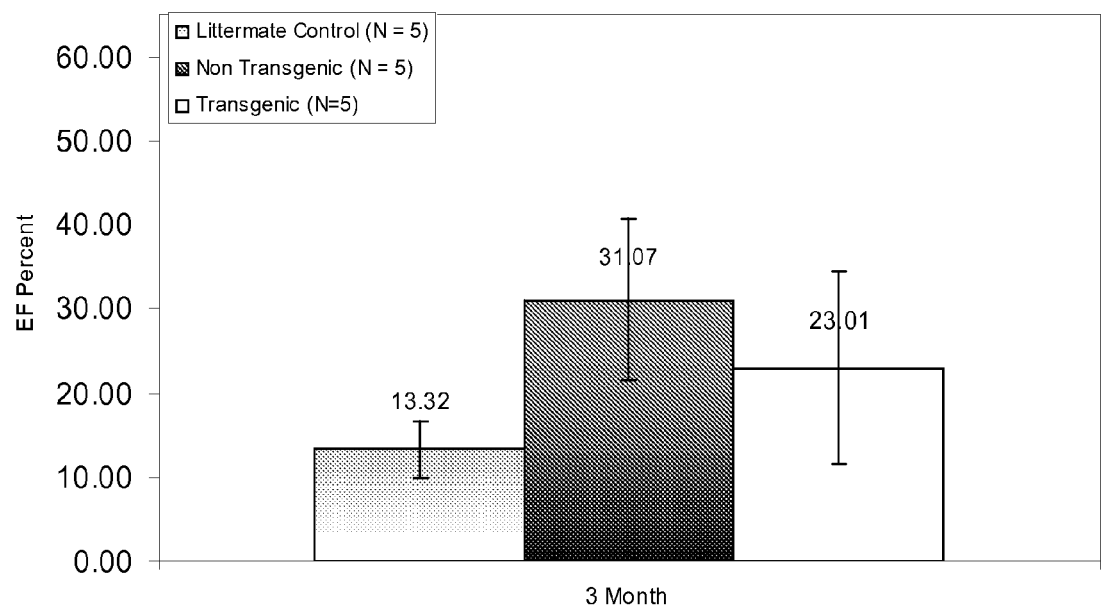
FIG. 6 is a bar graph showing ejection fraction percent in mice as determined by MRI at 3 months after myocardial transplant of transgenic cyclin A2 expressing side population stem cells, wild type side population stem cells, and controls. Further details regarding methodology are presented in Example 7.
Figure 7:
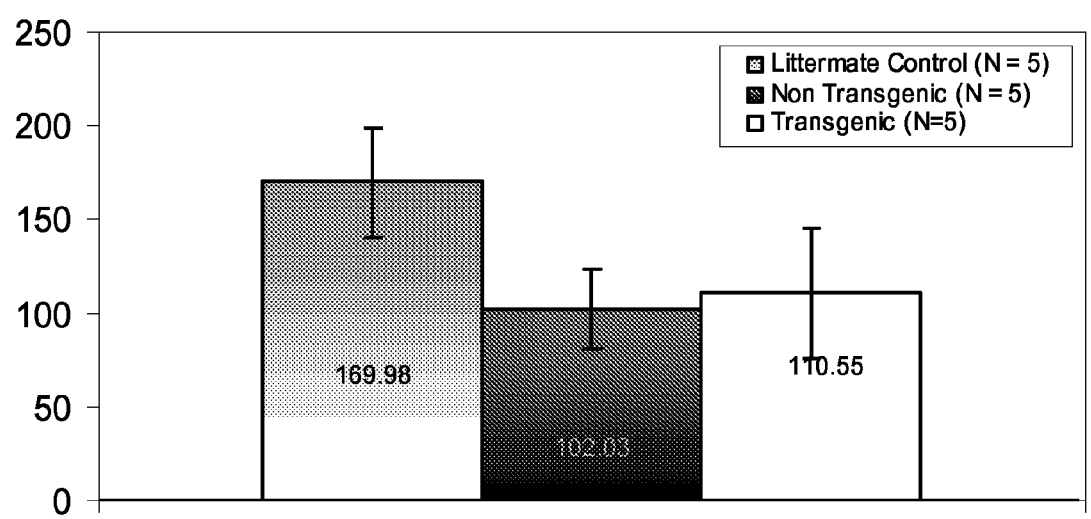
FIG. 7 is a bar graph showing end diastolic volume in mice hearts as determined by MRI at 3 months after myocardial transplant of transgenic cyclin A2 expressing side population stem cells, wild type side population stem cells, and controls. Further details regarding methodology are presented in Example 7.
Figure 8:
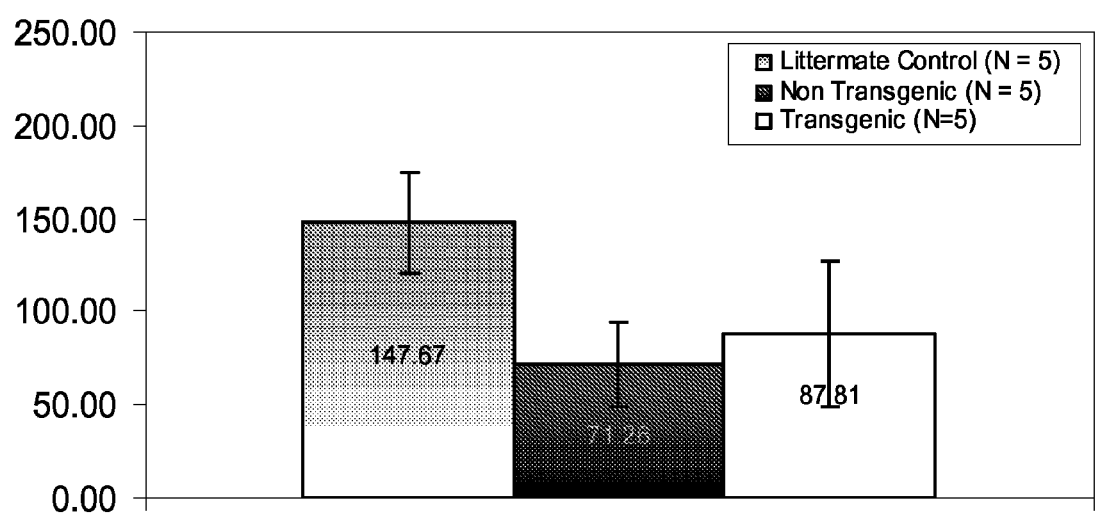
FIG. 8 is a bar graph showing end systolic volume in mice hearts as determined by MRI at 3 months after myocardial transplant of transgenic cyclin A2 expressing side population stem cells, wild type side population stem cells, and controls. Further details regarding methodology are presented in Example 7.

Results from MRI analysis showed that transplanted transgenic (cyclin A2 expressing) side-population cells (n=5) and non-transgenic side-population cells (n=5) both resulted in significantly elevated ejection fraction after 3 months as compared to controls (n=5) (see e.g., FIG. 6). Furthermore, transplanted transgenic side-population cells appeared to effect a larger increase in ejection fraction as compared to non-transgenic side-population cells. Results also showed that transplanted transgenic side-population cells and non-transgenic side-population cells both resulted in significantly decreased end diastolic volume (see e.g., FIG. 7) and end systolic volume (see e.g., FIG. 8) after 3 months.

Thus, greatest evidence of myocardial functional improvement is noted with the transplant of side-population cells engineered to express cyclin A2, with functional improvement also noted in transplant of wild-type side-population cells.

What is claimed is:

1. A method for restoring cardiac function in a subject in need thereof comprising:
    isolating side-population (SP) cells from bone marrow of a subject by gating on Hoechst 33342 dye, wherein the SP cells comprise a nucleic acid sequence encoding an exogenous (pg 13, paragraph 46) cyclin A2 and express the cyclin A2;
    introducing the SP cells into a region of myocardial infarction in a heart of the subject such that ejection fraction of the heart improves.

2. The method of claim 1 wherein the composition further comprises a pharmaceutically acceptable carrier.

3. The method of claim 1 wherein the subject is an animal.

4. The method of claim 3 wherein the subject is a mammal.

5. The method of claim 4 wherein the subject is a human.

6. The method of claim 1 wherein the amount of introduced composition comprises about $1 \times 10^8$ to about $1 \times 10^2$ side population cells.

7. The method of claim 6 wherein the amount of introduced composition comprises about $1 \times 10^6$ to about $1 \times 10^5$ side population cells.

8. The method of claim 1, wherein the side-population cells have been isolated by gating on Hoechst 33342 dye via fluorescent activated cell sorting.

9. A method for restoring cardiac function in a subject in need thereof comprising:
    isolating side-population (SP) cells from bone marrow of a subject by gating on Hoechst 33342 dye, wherein the SP cells comprise a nucleic acid sequence encoding an exogenous cyclin A2 and express the cyclin A2;
    introducing the SP cells into a region of peri-infarct in a heart of the subject such that ejection fraction of the heart improves.

* * * * *